(12) United States Patent
Garbow

(10) Patent No.: US 10,774,360 B2
(45) Date of Patent: Sep. 15, 2020

(54) METHOD FOR DETERMINING THE NUMBER OF SITES OF INFECTION OF A CELL CULTURE

(71) Applicant: PerkinElmer Cellular Technologies Germany GmbH, Hamburg (DE)

(72) Inventor: Norbert Garbow, Hamburg (DE)

(73) Assignee: PerkinElmer Cellular Technologies Germany GmbH, Hamburg (DE)

( * ) Notice: Subject to any disclaimer, the term of this patent is extended or adjusted under 35 U.S.C. 154(b) by 0 days.

(21) Appl. No.: 16/304,407

(22) PCT Filed: May 24, 2017

(86) PCT No.: PCT/EP2017/062617
§ 371 (c)(1),
(2) Date: Nov. 26, 2018

(87) PCT Pub. No.: WO2017/202956
PCT Pub. Date: Nov. 30, 2017

(65) Prior Publication Data
US 2019/0292578 A1 Sep. 26, 2019

(30) Foreign Application Priority Data

May 27, 2016 (EP) .................................. 16171730

(51) Int. Cl.
| | | |
|---|---|---|
| *A61K 39/00* | (2006.01) | |
| *A61K 39/12* | (2006.01) | |
| *C12N 7/00* | (2006.01) | |
| *C07K 14/005* | (2006.01) | |
| *C12N 15/86* | (2006.01) | |
| *C12Q 1/04* | (2006.01) | |
| *G01N 21/59* | (2006.01) | |
| *G01N 21/64* | (2006.01) | |
| *G01N 33/569* | (2006.01) | |

(52) U.S. Cl.
CPC .............. *C12Q 1/04* (2013.01); *G01N 21/59* (2013.01); *G01N 21/6428* (2013.01); *G01N 33/56983* (2013.01); *G01N 2021/6439* (2013.01)

(58) Field of Classification Search
CPC .. A61K 2300/00; A61K 39/12; C07K 14/005; C12N 7/00; C12N 15/86
See application file for complete search history.

(56) References Cited

U.S. PATENT DOCUMENTS 6,610,474 B1 8/2003 Huang

FOREIGN PATENT DOCUMENTS

| DE | 10332117 A1 | 12/2004 |
|---|---|---|
| WO | 9112337 A1 | 8/1991 |
| WO | 2011094445 A1 | 8/2011 |
| WO | 2012050645 A2 | 4/2012 |
| WO | 2015005961 A1 | 1/2015 |

OTHER PUBLICATIONS

Hodes et al., "shope fibroma virus assay based on enumeration of cells containing inclusion bodiies", 1968, Virology, 34(1):134-140.*
Cambier et al., "Quantitative Assay of Paravaccinia Virus Based on Enumeration of Inclusion-Containing Cells", Applied Microbiology, Jul. 1972, pp. 138-142, vol. 24:1.
Hodes et al., "Shope Fibroma Virus Assay Based on Enumeration of Cells Containing Inclusion Bodies", Virology, 1968, pp. 134-140, vol. 34.
Klebe et al., "A Technically Simple 'Non-Lethal' Vital Staining Procedure for Viral Plaque and Cell Transformation Assays", Archives of Virology, 1984, pp. 359-362, vol. 81.
Kuzikov et al., "Determination of Transfection Efficiency using the EnSight Multimode Plate Reader," Perkin Elmer, Mar. 2016, pp. 1-4.

* cited by examiner

*Primary Examiner* — Barry A Chestnut
(74) *Attorney, Agent, or Firm* — The Webb Law Firm

(57) ABSTRACT

Provided herein is a method for determining the number of sites of infection of a cell culture, including the steps of: infecting a cell culture arranged in a sample carrier with viruses, counting any infected areas of the cell culture by means of a transmitted light method, marking infected cells with fluorescence markers, counting infected areas of the cell culture by means of a fluorescence analysis method, and evaluating area by area the areas determined in both methods for determining the number of sites of infection.

16 Claims, 1 Drawing Sheet

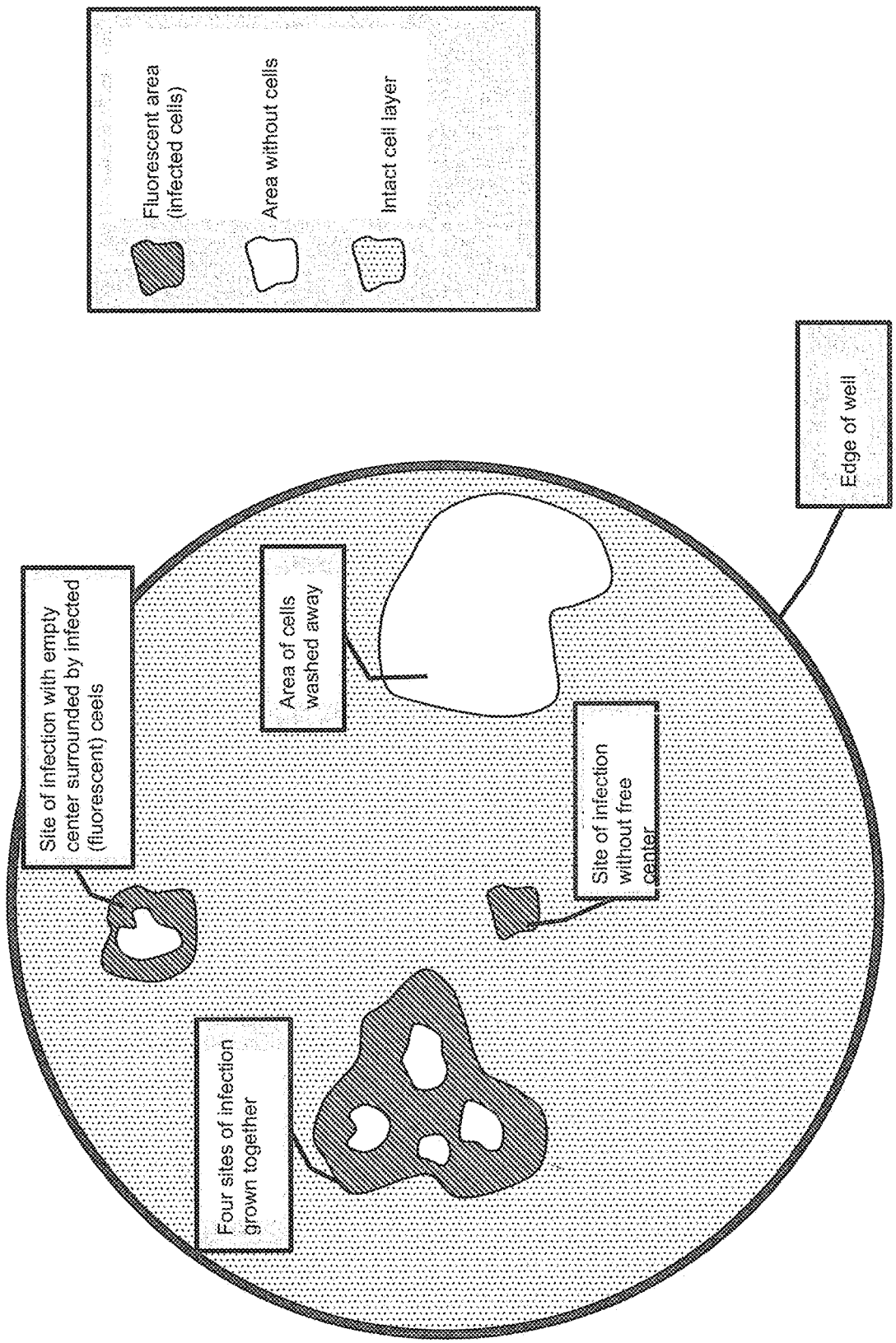

METHOD FOR DETERMINING THE NUMBER OF SITES OF INFECTION OF A CELL CULTURE

CROSS-REFERENCE TO RELATED APPLICATIONS

This application is the United States national phase of International Application No. PCT/EP2017/062617 filed May 24, 2017, and claims priority to European Patent Application No. 16171730.1 filed May 27, 2016, the disclosures of which are hereby incorporated in their entirety by reference.

BACKGROUND OF THE INVENTION

The invention relates to a method for determining the number of sites of infection of a cell culture.

For determining the number of sites of infection of a cell culture, it is known to first grow a cell culture on a sample carrier. Suitable sample carriers are in particular titer plates and microtiter plates, wherein cell cultures are grown in the individual wells so that the cells can attach to the well bottom. Thereafter, the cells are infected with a viral liquid. The same is usually diluted, with viral liquids of different dilutions being added to different wells. After a predetermined period, which depends in particular on the type of virus, the viral liquid is removed, in particular pumped off. The viral liquid usually acts on the cell culture for several minutes to several hours. After removal of the viral liquid, a medium is usually supplied that is to prevent a diffusion of virus particles released at a later time. Such a medium, which is introduced in particular as a gel layer, is used to cover the cell culture. Thereafter, a longer period of typically several days of waiting occurs. During this period, the infected cells die and the viruses emerging therefrom spread into the adjacent cells. Thereby comparatively large areas are formed in which dead cells are no longer visible and are surrounded by zones with cells that are still alive but already infected. Here, sites of infection are defined as areas on the sample carrier in which an initial infection of the cells by the virus has taken place, wherein, starting from the respective site of infection, infected areas are formed in which the cells are already infected and/or have already been destroyed.

Using a transmitted light method, it is possible to count the destroyed areas or areas in which no living cells are left. Such counting is typically performed after taking a respective image by persons, by photography or microscopy. If necessary, the sample may be stained with a dye for an increase in contrast. A suitable, in particular unspecific dye, such as e.g. methylene blue, marks the living cells so that the areas, in which no living cells exist, are more clearly obvious to the viewer as holes.

Determining the number of sites of infection of a cell culture by means of a transmitted light method in particular has the disadvantage that e.g. cells infected at a later time or cells reacting to the virus in a different way have not died yet and, as such, no corresponding hole can be seen using the transmitted light method. This also applies e.g. to cells that react more slowly, so that the corresponding holes are still very small and are therefore not visible or only with difficulty. It is another disadvantage of the transmitted light method that other voids that were not caused by the viruses, are detected as such voids and are erroneously included in the count. Such voids may e.g. areas in which the cells were washed away or in which contaminations exist. Washing away can occur e.g. when the viral liquids are added or when the gel is added. Further, the duration of the period which has to be waited prior to the transmitted light method being performed correspondingly, is difficult to determine and depends in particular on the type of the viruses. If the period is too short, the corresponding infected areas only have a small number of dead cells so that the corresponding holes or voids are difficult to discern. If the period is too long, individual areas grow to merge so that it is hard to determine, whether, originally, there was only one site of infection, or a plurality of sites of infection with a common infected area of the cell culture.

Further, for determining the number of sites of infection of a cell culture, it is known to treat the cell culture with in particular virus-specific fluorescence makers that mark the infected cells. It is then possible to count the infected areas, since the corresponding areas fluoresce. However, this method has a disadvantage in that adjacent infected areas cannot be discerned from each other and can therefore only be detected erroneously as one original site of infection.

SUMMARY OF THE INVENTION

It is an object of the invention to provide a method for determining the number of sites of infection of a cell culture, with which the number of sites of infection can be determined more exactly and more reliably.

The object is achieved according to the invention with a method as defined in claim 1.

BRIEF DESCRIPTION OF THE DRAWINGS

FIG. 1 shows a schematic view of a well of a titer plate.

DESCRIPTION OF THE INVENTION

In the method for determining the number of sites of infection in a cell culture, as provided by the invention, first a cell culture arranged in a sample carrier is infected with viruses. This is done in particular by adding a viral liquid which may be diluted, if so desired. Here, sites of infection are defined as areas on the sample carrier in which an initial infection of the cells by the virus has taken place, wherein, starting from the respective site of infection, infected areas are formed in which the cells are already infected and/or have already been destroyed. Titer plates, in particular microtiter plates are preferably used as sample carriers, the cell cultures preferably having grown on the well bottom.

In the next step, the known transmitted light method is used to determine possibly infected areas in which a hole has already been formed in the cell culture due to a destruction of the cells by the virus infection. Thus, using the transmitted light method, all areas are determined in which no living cells exist. Accordingly, corresponding voids or holes are determined. In doing so, in particular not only those areas are determined in which cells have died due to the virus, but also those areas which include no living cells due to contaminations or because cells have been washed away.

Further, according to the invention, infected cells are marked using an in particular specific fluorescent marker. Here, the infected cells are marked directly based on the virus and/or based on an effect caused directly by the virus. In this manner, the infected areas can be discerned from the non-infected areas of the cell culture. The infected areas of the cell culture are then determined using fluorescence analysis methods. In doing so, large fluorescent areas are at least initially also counted as only one area.

Subsequently, the two methods are combined as provided by the invention, such that the areas determined by the two methods are evaluated area by area, in order to determine the number of sites of infection. In particular, all areas determined before either by the transmitted light method or by a fluorescence analysis method are consecutively sifted through, and the respective number of sites of infection of the respective area considered is reliably determined from the combination of the two methods. It would be possible, for example, to sum up the areas determined in the two methods. Since, in this case, individual areas are counted twice, a matching can be performed in particular by superposing the determined results of the transmitted light method and the fluorescence analysis method regarding the determined areas, such that the areas determined by both methods are counted only once. Thus, for example, only such areas can be counted as sites of infection, which have been identified as sites of infection by both methods. Specifically, areas also detected by the fluorescence analysis method which, according to the transmitted light method, include a plurality of sites of infection, can reliably be characterized as multiple infections. If only thereby, the accuracy of determining the number of sites of infection in a cell culture is improved significantly.

In particular, the sequence of the method steps, i.e. applying of the transmitted light method as described above, marking the infected cells using a specific marker as described above, and applying the fluorescence analysis method as described above, is optional, wherein, of course, a marking of the infected cells has to be performed always prior to the fluorescence analysis method. Thus, it is possible, for example, to mark the infected cells of the sample using a specific marker and to subsequently perform the transmitted light method and the fluorescence analysis method. In this regard, it is particularly preferred to perform the transmitted light method and the fluorescence analysis method simultaneously on the sample.

In a preferred development of the method according to the invention, the evaluation of the areas determined by means of the two methods is effected such that areas detected by the transmitted light method, which, however, were not detected by the fluorescence analysis method, are not counted as a site of infection. By a comparison of the areas determined by means of the two methods, it is possible to determine voids or holes that were not caused by the viral infection, since such voids are not surrounded by fluorescent, i.e. virally infected cells. Accordingly, using the method of the invention, it is possible to separately determine voids which were formed e.g. by washing away or contaminations, so that these do not corrupt the result of the number of sites of infection. In particular, it is also possible to count or evaluate these areas separately. This allows for a quality control of the sample. For example, in case of a predetermined number of such imperfections where the contaminations, the washing of cells or the like have occurred, it is possible to disregard the corresponding sample during evaluation. This can be done in particular in an automatic manner based on the number or the size of the corresponding voids. Controlling the frequency and the size of these imperfections is also of importance for the quality control of the sample preparation.

In another preferred embodiment of the invention areas are determined that are detected by the fluorescence method, but not in the transmitted light method. These areas are counted as sites of infection of the cell culture. These areas are areas which have virus-infected cells in which, however, the cells are not yet damaged to an extent that a corresponding number of dead cells is present, which would then also decompose and would be detectable as an empty area by the transmitted light method. In particular, it is also possible to count and even weigh these areas. This analysis may be feasible e.g. to obtain indications of strongly varying infection speeds of the viruses. Further, a quality control of certain aspects of sample preparation is possible thereby.

In another preferred embodiment of the invention, the areas detected in particular by both methods are analyzed for their size and/or shape. Specifically, when a predefined limit size is exceeded, i.e. when a predefined extent or a predefined surface area of the infected area is exceeded, the corresponding area can be counted several times. This is based on the assumption that this area is formed by a plurality of original sites of infection that have grown together.

Preferably, such areas are analyzed more thoroughly. Thus, for areas detected by the fluorescence analysis method and exceeding a predefined limit size, a number of sites of infection is defined depending on the size, the shape and/or the fluorescence intensity. Further, it is possible to analyze these areas more thoroughly by considering the number of voids. The number of voids that according to the fluorescence are due to dead cells, preferably is the minimum number of the sites of infection originally infected in this area. This number may possibly be increased due to the strong fluorescence, since it has to be assumed that initially infected cells are also present in this area which have not died yet so that no void has formed.

Preferably, the limit size is defined in dependence on the samples and/or on the measurements. For example, it is possible to determine the limit size on the basis of a size distribution of the corresponding areas found. It would also be possible, e.g., to perform a comparison with the median value of such areas found. Specifically, a determination of the limit value can be made based on a statistic of sizes of the different areas.

It is particularly preferred to perform the transmitted light method and/or the fluorescence analysis method as automated methods. This is effected in particular on the basis of imaging methods. Automated microscopes or plate reading devices with image processing methods are particularly suitable for this purpose. For example, the plate reader EnSight of the manufacturer PerkinElmer is suitable therefor.

For increasing the contrast in the transmitted light method, the cell culture can be stained. This may be done using methods and dyes known per se, in particular methylene blue. Specifically, staining the cell culture is done with an unspecific dye that stains all cells of the cell culture in the same manner, so as to make voids in the cell culture be clearly visible. Possibly, it is necessary to consider the spectral characteristics of the dye used in the fluorescence method. Further, similar to methods for determining the number of sites of infection of a cell culture of the prior art, the growth of the cells, the infection of the cells with a viral liquid, and the covering with a gel can be performed as known. In particular, the cell cultures can be infected using a viral liquid that may be diluted, if necessary. In this regard, it is preferred hat the factor of dilution is taken into account in the determination of the number of sites of infection. When using titer plates, in particular microtiter plates, it is further preferred that the same cell culture is present in each well and/or the same viral liquid is added, possibly in different dilutions. In particular, by using microtiter plates with a large number of wells, it is also possible to use different viral liquids or cell cultures treated with different pharmaceutic agents.

In a preferred development of the invention control values for quality control are determined in particular automatically. This may be a closer inspection or only a counting of the voids which are voids caused e.g. by washing or by contaminations and not by dead cells. Further, important control values are the quality of the object recognition, the texture of the cell layers which are in particular not affected by a virus infection, or the intensity of the specific infection marker averaged for a sample. In addition, details about the size or the morphology of the detected areas of infection can be used in interpreting the measurement.

Other unspecific detection methods may be used instead of a transmitted light method. Suitable methods for this purpose are fluorescence method which mark cells regardless of an infection and which are thereafter read out microscopically. To allow for a simple distinction from the infection-specific marking, a fluorescent dye with different characteristics (e.g. emission wavelength) is preferred for this purpose.

Likewise, it is possible to implement other infection-specific detection methods instead of a fluorescence analysis method. These use non-fluorescent infection-specific markers. For example, these may be dyes for colorimetric methods.

With suitable cell types, it may also be possible to distinguish areas of infected cells from non-infected cell areas without a special marker, based on the texture characteristics.

Further, it is possible to use this method not only for the examination of an infection of cell cultures by viruses. For example, it is conceivable to use it also with bacteria that infect cell cultures or with cells or (unicellular) beings such as amoebas that feed on bacteria cultures.

The accompanying drawing shows a well of a titer plate as a schematic example. In the area inside the well edge, a cell culture is arranged which, as described before, has been infected with viruses. As a result, different areas are formed. The area illustrated in white is an area in which cells have been washed away e.g. when the viral fluid or the like was added, and thus an area without cells is formed. The dark shaded areas are fluorescent areas, i.e. areas in which infected cells are present. In this case, different areas can be formed. In the example illustrated, this is an area without a free center. This is an area which contains infected cells, but in which no free center of dead cells has been formed.

In the top part of the drawing, an infected area is illustrated which has a free or empty center. The empty center is the area in which dead cells are present. These are surrounded by infected and therefore fluorescent cells. The large area shown on the left hand side of the well illustrates a site of infection that has grown together. The same has four empty centers surrounded by fluorescent and thus infected cells.

The invention claimed is:

1. A method for determining the number of sites of infection of a cell culture, the method comprising:
    infecting a cell culture arranged in a sample carrier with viruses;
    determining infected areas of the cell culture using a transmitted light method, thereby providing a transmitted light result;
    marking infected cells with fluorescence markers;
    determining infected areas of the marked infected cells using a fluorescence analysis method, thereby providing a fluorescence result; and
    determining the number of sites of infection by superimposing the transmitted light result and the fluorescence result and identifying the number of sites of infection based on the superimposing.

2. The method of claim 1, further comprising, separately counting areas that are identified by the fluorescence analysis method, but not by the transmitted light method.

3. The method of claim 1, further comprising counting several times areas that exceed a predefined limit size.

4. The method of claim 1, further comprising, depending on the size, shape and/or fluorescence intensity, defining a number for areas identified by the fluorescence analysis method and exceeding a predefined limit size.

5. The method of claim 1, wherein one or more areas identified by the fluorescence analysis method and exceeding a predefined limit size, are compared with the corresponding area of the area determined by the transmitted light method, and at least a number of the voids identified in these one or more areas are counted.

6. The method of claim 3, further comprising adjusting the predefined limit size depending on the samples and/or the measurements.

7. The method of claim 1, wherein the transmitted light method and/or the fluorescence analysis method are automatically executed.

8. The method of claim 1, wherein the cell cultures are dyed prior to execution of the transmitted light method.

9. The method of claim 1, wherein control values for quality control are determined automatically.

10. The method of claim 1, wherein the cell culture is infected using a viral liquid, optionally a diluted viral liquid.

11. The method of claim 10, wherein a dilution factor of the diluted viral liquid is taken into account in the determination of the number of sites of infection.

12. The method of claim 1, wherein a titer plate is used as the sample carrier.

13. The method of claim 12, wherein the same cell culture is present in each well of the titer plate.

14. The method of claim 11, wherein the diluted viral liquid is removed after a residence time and is replaced with a cover, which hinders a diffusion of virus particles released at a later time.

15. The method of claim 1, wherein the execution of the methods is performed after an incubation period of several minutes.

16. A system for determining the number of sites of infection of a cell culture, the system comprising:
    a sample carrier comprising a cell culture; and
    a plate reading device configured to perform a transmitted light analysis method and a fluorescence analysis method, wherein the plate reading device is further configured to:
        determine infected areas of the cell culture using the transmitted light method, thereby providing a transmitted light result;
        determine infected areas of infected cells using a fluorescence analysis method, thereby providing a fluorescence result; and
        determine the number of sites of infection by superimposing the transmitted light result and the fluorescence result and identifying the number of sites of an infection based on the superimposing.

* * * * *